United States Patent [19]

Harris, II

[11] Patent Number: 5,711,295
[45] Date of Patent: Jan. 27, 1998

[54] RESUSCITATION DEVICE

[76] Inventor: Robert E. Harris, II, 207A Lytle Rd., Rossville, Ga. 30741

[21] Appl. No.: 635,375

[22] Filed: Apr. 19, 1996

[51] Int. Cl.$^6$ .................................................. A61M 16/00
[52] U.S. Cl. ............................ 128/202.28; 128/203.11; 128/205.13
[58] Field of Search ........................ 128/202.28, 202.29, 128/203.11, 205.13; 601/41

[56] References Cited

U.S. PATENT DOCUMENTS

| | | | |
|---|---|---|---|
| 1,177,208 | 3/1916 | Pierpont | 128/202.28 |
| 3,425,409 | 2/1969 | Isaacson | 128/28 |
| 4,297,999 | 11/1981 | Kitrell | 601/41 |
| 4,349,015 | 9/1982 | Alferness | 128/28 |
| 4,397,306 | 8/1983 | Weisfeldt et al. | 601/41 |
| 4,446,864 | 5/1984 | Watson et al. | 128/202.28 |
| 4,870,962 | 10/1989 | Sitnik | 128/205.13 |
| 4,898,166 | 2/1990 | Rose et al. | 128/205.13 |
| 5,327,887 | 7/1994 | Nowakowski | 601/41 |
| 5,345,929 | 9/1994 | Jansson | 128/205.13 |

Primary Examiner—Aaron J. Lewis

[57] ABSTRACT

This is a device for resuscitation of asphyxiated or semi asphyxiated patients. It is used primarily by emergency rescue and ambulance personnel. It is designed to supplement equipment already in use and is not intended to replace other equipment. It comprises manually operable mechanical equipment to replace the use of a medic's hand, presently used to squeeze and release a plastic air bag (10) which in turn alternately forces air or oxygen into the lungs of the patient and releases carbon dioxide and other waste gases from the lungs of the patient. The resuscitation device holds the plastic bag between a stationary mechanical upper hand (36) and a vertically moveable mechanical lower hand (56). The vertical movement of the lower hand is sustained by a pivotable lever (70) which is manually operated by rescue personnel. The pivotable lever gives the rescue personnel substantial mechanical advantage and leverage for sustaining the pumping action of the standard equipment used to force air or oxygen into the lungs of the patient and to release waste gases from the lungs of the patient. This device prevents the air bag from being accidentally moved during rescue efforts. It provides the rescue personnel with the assurance of knowing where the air bag is located at all times during hectic rescue efforts. When the rescue personnel must remove his hand temporarily from the pivotable lever to perform other life saving tasks, he can quickly return to the task of moving the lever up and down to provide respiratory support.

2 Claims, 2 Drawing Sheets

RESUSCITATION DEVICE

BACKGROUND-FIELD OF INVENTION

This invention relates to respirators which are used for providing a mixture of air/oxygen to asphyxiated or semi-asphyxiated medical patients, and specifically to such respirators as are manually operated.

BACKGROUND-DESCRIPTION OF PRIOR ART

Paramedics and emergency medical technicians must frequently provide respiratory support to patients whose breathing is inadequate. The device most commonly used is known as a bag, valve, mask apparatus, commonly known as a BVM, which consists of an air bag which can be manually compressed, forcing air through a valve and into a mask, which covers the patient's nose and mouth. Often, especially in case of severe head trauma, an endotracheal tube will be inserted into the trachea through the nose or throat, in which case the mask will be eliminated. In such cases, it is very important that the patient be immobilized and that the endotracheal tube be attached in such a way as to ensure that it is not moved during the process of providing respiratory support. The air bag is available in a variety of sizes, enabling the rescue worker to select a size which corresponds to the patient's lung capacity.

Emergency respiratory support is frequently rendered by paramedics, emergency medical technicians, firefighters, and police, who require a device which is portable, manually operable, lightweight, versatile and simple. Such respiratory support is often required when transporting patients by ambulance or helicopter, situations in which there may be only one rescue worker available to care for the patient. This single rescue worker may be required to control the patient's bleeding, to administer drugs, to communicate with other emergency workers regarding the patient's condition, and to perform any other actions that the patient's health may require. The bag, valve, mask apparatus (BVM), currently the standard device used in such situations, requires the use of both hands to operate properly, is exhausting to the operator if used for more than a short period of time, and prevents the operator from performing other tasks. The air bag must always be secured by the rescue worker to prevent the possibility of a loose air bag disturbing the tube connection to the patient's face or throat.

Prior to the widespread acceptance of the BVM as the standard device for providing emergency respiratory support, several other methods of forcing air into the patient's lungs were developed. U.S. Pat. No. 1,197,232 issued to Pierpoint (1916) discloses a hand operated bellows which forces air through a valve into a face mask. A number of improvements have been made to Pierpoint's invention. U.S. Pat. No. 3,196,866 to Adams (1965) discloses the use of an elastic air bag which is self-inflating due to its football shape. Flynn, in U.S. Pat. No. 4,532,923, (1985) discloses an improved air bag utilizing a ribbed design to increase the speed with which the bag self-inflates. U.S. Pat. No. 4,870,962 to Sitnik (1989) discloses a wedge-shaped bellows made of plastic materials, the compressible walls of which incorporate a pleated design to promote rapid self-inflation.

In 1990, U.S. Pat. No. 4,898,166 was issued to Rose et al., disclosing a device which holds an air bag within a frame which is used to compress the air bag. An adjustable strap is used to limit the maximum size to which the air bag can self-inflate, thus giving the operator more control over the amount of air flow to the patient. The device was also intended to provide some degree of mechanical advantage to the operator, so as to reduce operator fatigue. However, it would still require two hands to operate, and the mechanical advantage available through the Rose design is quite limited.

U.S. Pat. No. 5,345,929 to Jansson et al. (1994) discloses a bellows-type resuscitation device which consists of a bellows contained within a carrying case, which may be operated by alternately opening and closing the lid of the case. This invention incorporates a projection which can prevent the lid from being entirely closed, thus limiting the maximum amount of air which would be pumped into the patient's lungs. Like the Rose device, supra, the amount of mechanical advantage provided by the Jansson device is insignificant, and would not prevent operator fatigue.

The BVM which is now in common use offers an additional advantage over the bellows-type design such as was incorporated in the Jansson device. Being made of inexpensive plastic or silicone materials, the BVM is disposable, thus eliminating the risk of transmission of disease and the necessity to sterilize parts of the resuscitation device prior to use.

A number of inventions have been developed which both provide an air supply to the patient and perform chest compressions to circulate the blood. U.S. Pat. No. 3,425,409 to Isaacson et al (1969) discloses a device for performing compressions on the patient's chest to circulate the blood. The device also accumulates air into a chamber and periodically releases the air through a pressure valve into a mask which is held over the patient's face. This device is not suitable when chest compressions are not required, nor when contact with the patient's chest must be avoided due to the nature of the injury. Since the device attaches to the patient's chest, it requires the complete immobilization of the patient in a supine position. Moreover, the device uses a complex system of gears and valves to regulate the discharge of air to the patient's lungs, which eliminates the tactile feedback needed by the operator.

U.S. Pat. No. 4,349,015 to Alferness (1982) discloses a device similar to that developed by Issacson et al (supra) in that it attaches to the patient's chest and is intended to increase blood circulation by compressing the chest cavity while pumping air into the patient's lungs. This device also compresses the abdominal cavity as a means of increasing blood circulation. Like the Issacson device, this device is unsuitable when chest compressions are not necessary or when contact with the patient's abdomen or chest are to be avoided. It is also deficient in that it requires the immobilization of the patient in a supine position so that downward pressure may be exerted on the patient's chest.

Although the design of the BVM has been improved in many ways since the original bellows design of Pierpoint, supra, there are still many difficulties in the proper use of the bag, valve, mask apparatus:

(a) the BVM requires two hands to operate. The air bag is too large to compress fully with one hand. Unless two hands are used, the rescuer will be unable to compress the air bag sufficiently to pump the correct amount of air into the patient's lungs. This is a serious deficiency, since the rescuer may be required to use one hand to maintain the face mask in its proper location, or to provide other care necessary for the patient's survival;

(b) the BVM is exhausting to operate. The force required to compress the air bag must also be sufficient to inflate the patient's lungs, and this considerable effort will exhaust the rescuer if maintained for more than a few minutes. Yet rescuers may be required to maintain breathing support for long periods of time as the patient is transported by ambulance, situations in which the rescuer is typically working without assistance due to the limited space available;

(c) the BVM will provide an inconsistent quantity of air to the patient when the rescuer is fatigued or unable to use both hands to compress the air bag;

(d) the BVM, when used with an endotracheal tube, can result in serious injury to the patient if the endotracheal tube is not immobilized with respect to the patient. Yet when the BVM is being held and operated manually by the rescuer, there is a substantial risk that the endotracheal tube may be pulled from its proper position. This can result in serious injury to the vocal chords, as well as loss of respiratory support.

OBJECTS AND ADVANTAGES

Accordingly, several objects and advantages of the present invention are:

(a) to provide a means for holding the BVM which will not require the use of the operator's hands, so that the rescuer will be able to perform other tasks;

(b) to provide a means for holding the BVM in a secure manner with respect to the patient, so that accidental movement of the BVM is prevented;

(c) to provide a means for compressing the air bag consistently and completely, so that the proper amount of air is provided to the patient;

(d) to provide a means for compressing the air bag using a lever to provide a mechanical advantage, so as to prevent operator fatigue;

(e) to provide a means for compressing air bags of a variety of sizes, so that the correct amount of air is provided in all cases;

(f) to provide a means for compressing air bags which provides tactile feedback to the operator, so that he may correctly judge the effectiveness of the respiratory support;

(g) to provide a means for respiratory support which enhances the utility of the BVM, a device which is disposable, readily available, standardized, and widely used;

(h) to provide a means for respiratory support which is portable, rugged, simple to operate, and affordable;

(i) to provide a means for respiratory support which can be positioned in a variety of ways with respect to the patient, so as to enable its use in crowded conditions such as inside an ambulance or helicopter;

(j) to provide a means for respiratory support which will increase the chance of patient survival.

Still further objects and advantages will become apparent from a consideration of the following descriptions and drawings.

DRAWING FIGURES

FIG. 1 also shows in outline the location of the BVM when the resuscitation device is in use.

Figure 1:
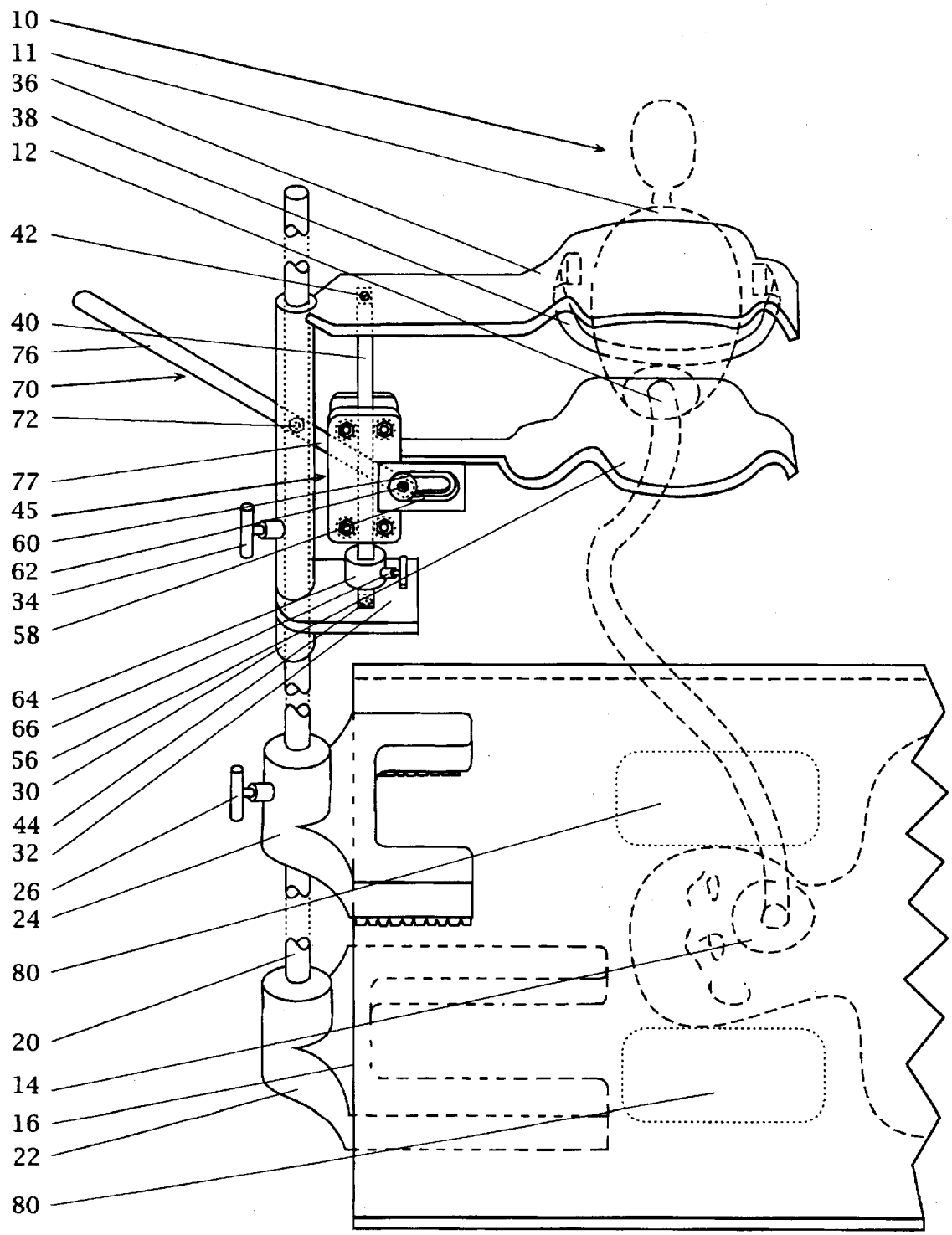
FIG. 1 is a perspective view of a preferred form of a resuscitation device.

REFERENCE NUMERALS IN DRAWINGS 10 bag, valve, mask apparatus (BVM)
11 air bag
12 flexible air tube
13 endotracheal tube (not shown)
14 air mask
16 backboard/bed
20 vertical column
22 bottom horizontal clap segment/base
24 upper horizontal clap segment
26 set screw for securing upper clap segment
30 vertical tubular body slidably mounted on vertical column 20
32 horizontal platform integral to tubular body 30
34 set screw for securing vertical tubular body 30
36 upper horizontal hand integral to tubular body 30
38 elastic or velcro strap
40 square shaped vertical post
42 screw securing vertical post 40 to upper horizontal hand 36
44 screw securing vertical post 40 to horizontal platform 32
45 conveyor mechanism
46 front cover of conveyor 45
48 back cover of conveyor 45
50 roller bearing
52 bearing stem
56 lower horizontal hand integral to conveyor 45
58 boxed horizontal twin bearing races
60 twin roller bearings (FIGS. 2 & 3)
62 bearing stem for bearings 60
64 slidable stop
66 set screw securing slidable stop 64
70 hand lever
72 shoulder screw pivot pin
76 handle end of lever 70
77 lower end of lever 70
78 weldment
80 cervical immobilization device

DESCRIPTION, FIGS. 1, 2 & 3

FIG. 1 shows a round vertical column 20, of predetermined size and height. A bottom horizontal clamp segment 22, integral to column 20, is located at the lower end of column 20. An upper horizontal clamp segment 24 is slidably mounted on column 20 just above bottom clamp segment 22 and is held fixed at predetermined locations on column 20 by common set screw 26.

A vertical tubular body 30 is slidably mounted on vertical column 20. A common set screw 34 located on vertical tubular body 30 holds vertical tubular body 30 securely on vertical column 20. A horizontal platform 32 is integral to the lower end of vertical tubular body 30. An upper horizontal hand 36 is integral to the upper end of vertical tubular body 30. A square shaped vertical post 40 is attached to the underside of upper horizontal hand 36 by means of screw 42, and is attached to the top side of horizontal platform 32 by means of screw 44 at a predetermined location such that square vertical post 40 is parallel to vertical tubular body 30. A shoulder screw pivot pin 72 extends horizontally from vertical tubular body 30.

A conveyor mechanism 45 is slidably mounted on square shaped vertical post 40. A lower horizontal hand 56 is integral to conveyor mechanism 45. A lever 70 is pivotally attached by bearing stem 62 to twin roller bearings 60 which run in twin horizontal bearing races 58. A hand lever 70 is pivotally attached to vertical tubular body 30 by pivot pin 72. A slidable stop 64 is slidably mounted on vertical post 40, and limits the downward motion of conveyor mechanism 45. Slidable stop 64 is held fixed at a predetermined location on vertical post 40 by a common set screw 66.

A bag, valve, mask apparatus 10 is shown in outline form in FIG. 1, and is attached to upper horizontal hand 36 by an elastic or velcro strap 38. Air tube 12 extends from air bag 11 to air mask 14. Apparatus 10 is available in various sizes to accommodate the lung capacity of the patient.

Figure 2:
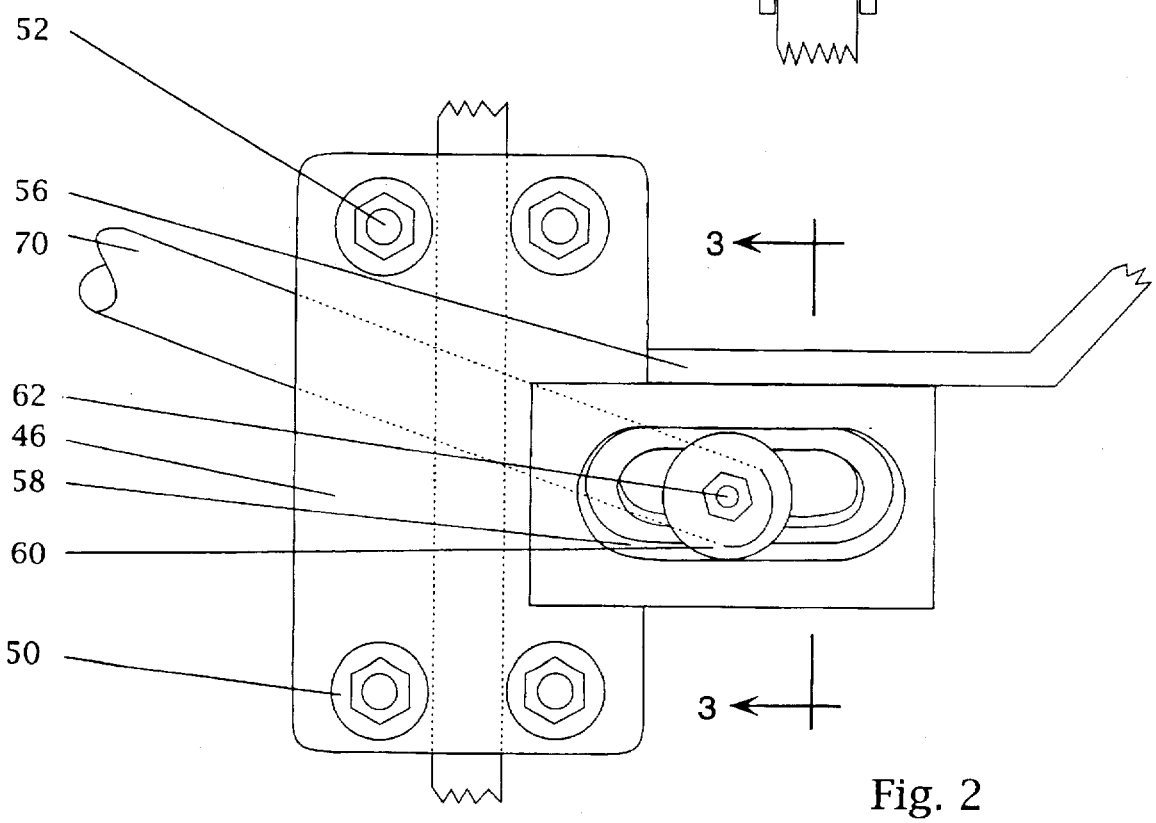
FIG. 2 is a front view of the conveyor mechanism 45, which constrains the motion of lower horizontal hand 56.

FIG. 2 shows conveyor mechanism 45. A front cover 46 and a back cover 48 (shown in FIG. 3), are integral to boxed horizontal twin bearing races 58, such that front cover 46 and back cover 48 are parallel. Four roller bearings 50 are mounted on four bearing stems 52 in predetermined locations between front cover 46 and back cover 48, and are secured in place by nuts 54. Square vertical post 40 extends between the upper pair of roller bearings 50 and between the lower pair of roller bearings 50. Twin roller bearings 60 are mounted in twin bearing races 58 by means of bearing stem 62. The lower end 77 of lever 70 is pivotally attached to bearing stem 62. Lower horizontal hand 56 is integral to conveyor mechanism 45. FIG. 2 also shows the location and orientation of section view A—A.

Figure 3:
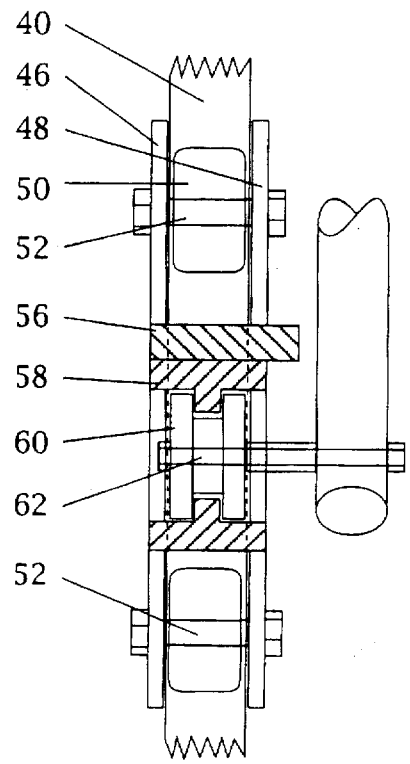
FIG. 3 is a cross-sectional view of conveyor mechanism 45 taken at -3—3- in FIG. 2.

FIG. 3 is a cross-sectional view taken at -3—3- in FIG. 2. Square shaped vertical post 40 extends between front cover 46 and back cover 48. Roller bearings 50, mounted on bearing stems 52, bear upon vertical post 40. Twin roller bearings 60 are mounted upon bearing stem 62, and run in twin bearing races 58. Lower horizontal hand 56 is integral to twin bearing races 58, being attached by weldmerits or fasteners. The lower end 77 of hand lever 70 is pivotally attached to bearing stem 62.

OPERATION

The operation of the resuscitation device herein described is best illustrated with reference to FIG. 1.

A medical patient in need of respiratory support is placed upon a table or backboard 16 made of rigid material to which the resuscitation device may be clamped. To prevent movement of the patient's head, standard cervical immobilization devices 80 are attached to backboard 16 by means of velcro fasteners (not shown). The bottom horizontal clamp segment 22 is placed beneath the backboard 16. The operator manually loosens set screw 26 sufficiently to allow upper horizontal clamp segment 24 to slide down vertical column 20 until upper horizontal clamp segment 24 is in firm contact with backboard 16. The operator next adjusts set screw 26 so that upper horizontal clamp segment 24 is prevented from sliding on vertical column 20. The resuscitation device is now securely clamped to the backboard 16.

A suitable bag, valve, mask apparatus 10 is attached to upper horizontal hand 36 by means of elastic or velcro strap 38. Lower horizontal hand 56 is manually raised by lever 70 to a position in contact with air bag 11. Slidable stop 64 is manually raised to a position in contact with conveyor mechanism 45. Common set screw 66 is tightened to prevent slidable stop 64 from sliding against vertical post 40. The range of motion of lower horizontal hand 56 is now limited to the range appropriate for the selected bag, valve, mask apparatus 10.

The resuscitation device is now ready for use. The operator must secure a good air seal with the air mask, or must insert an endotracheal tube; these operations are not described herein. To operate the resuscitation device, the operator manually causes the handle end 76 of hand lever 70 to move downward. The resultant upward motion of lower end 77 of hand lever 70 causes bearing stem 62 to move upward. Twin roller bearings 60 mounted upon bearing stem 62 bear upon twin bearing races 58 and cause conveyor mechanism 45 to move upward. The motion of conveyor mechanism 45 is constrained by square vertical post 40 so that the motion of conveyor mechanism 45 is co-axial to vertical column 20. Lower horizontal hand 56, integral to conveyor mechanism 45, remains parallel to upper horizontal hand 36.

As a result of the upward motion of lower horizontal hand 56, air bag 11 is compressed, and the air/oxygen contained in air bag 11 is forced through air tube 12 into air mask 14.

When the operator determines that air bag 11 has been sufficiently compressed, he allows the handle end 76 of lever 70 to move upward. The upward motion of handle end 76 of lever 70 allows conveyor mechanism 45 to move downward until conveyor mechanism 45 is in contact with slidable stop 64. Lower horizontal hand 56, which is integral to conveyor mechanism 45, moves downward and remains parallel to upper horizontal hand 36. Air bag 11 is no longer compressed, and will self-inflate.

The cycle of compressing and inflating the air bag 11 can be continued indefinitely. Since the bag, valve, mask apparatus 10 is held in place by the upper horizontal hand 36, the operator can release the handle 76, if necessary for the performance of other tasks, without causing the accidental movement of the bag, valve, mask apparatus 10.

The position of the medical patient on the backboard 16 does not affect the operation of the resuscitation device described herein; the patient may be prone, supine, or lying on either side, provided that the operator is able to maintain a secure air seal with air mask 14, or has inserted an endotracheal tube. Similarly, the vertical tubular body 30 may be rotated co-axially on vertical column 20 without affecting the operation of the resuscitation device. This allows the resuscitation device to be used in a wide variety of positions relative to the patient.

The invention herein described may be constructed from a wide range of materials, including steel, aluminum, titanium, or other rigid metals, as well as plastics and other synthetic materials.

SUMMARY, RAMIFICATIONS AND SCOPE

Accordingly, the reader will see that the resuscitation device herein described will securely hold the bag, valve, mask apparatus, so that the operator can perform other tasks. This invention will provide a mechanical advantage which will prevent operator fatigue, even when respiratory support must be continued for long periods of time. The upper and lower horizontal hands, which compress the BVM, are optimally shaped to compress the selected BVM fully, so that the correct amount of oxygen is provided to the patient at all times.

The invention described herein is portable, rugged, simple to operate, and affordable. The simplicity of its design provides the operator with important tact fie feedback, which allows the operator to judge correctly the effectiveness of the respiratory support. The invention utilizes and greatly extends the effectiveness of the standard BVM. It can be mounted and used in a wide variety of positions, and can easily be used within confined spaces such as ambulances and helicopters.

Although the description of the invention has used several illustrations to show a preferred embodiment of the invention, these illustrations should not be construed as limiting the scope of the invention. Rather, the scope of the invention is to be determined by the appended claims, or their legal equivalents.

I claim:

1. A resuscitation device for resuscitating a patient, comprising a an apparatus comprising
 a' an air bag of predetermined size
 b' a valve of predetermined size
 c' a mask of predetermined size
 d' an endotracheal tube of predetermined size,
said mask and said endotracheal tube being capable of being secured to said patient and being securely joined to said bag and to said valve by tubing of predetermined size and length, b a bed for supporting the patient, c a supply of air and a supply of oxygen d manually operable mechanical means for safely securing said apparatus in conjunction with said patient, and alternately compressing and releasing the air bag whereby a predetermined amount of air or oxygen is alternately forced into and released from a patient's lungs, said mechanical means comprising
 a' a portable stand comprising
  a" a vertical column,
  b" a bottom horizontal clamp segment
  c" a vertically movable, slidably mounted upper horizontal clamp segment,
  d" means for securing said upper horizontal clamp to said vertical column at predetermined locations, said vertical column, being of predetermined size and length, and being integral to said bottom horizontal clamp segment, extends upward from said bottom clamp segment through said upper horizontal clamp segment,
 b' means for clamping said stand to the bed,
 c' a slidable carriage comprising
  a" a tubular body of predetermined size and length having a base and having an upper end integral thereto and being mounted on said column
  b" a horizontal flat platform having a top surface comprising a central area, said platform of predetermined dimensions, integral to said tubular body, and located at the base of said tubular body,
  c" an upper horizontal hand having a bottom surface, integral to said tubular body and located at the upper end of said tubular body,
  d" straps attached to the bottom surface of said upper horizontal hand,
  a square shaped vertical post of predetermined size and length located in the central area of the top surface of said platform and extending vertically to the bottom surface of said upper horizontal hand,
  e' means for releasably securing said post to said platform and to said upper hand,
 f' a rectangularly shaped conveyor comprising
  a" a plurality of bearings having bearing stems
  b" a front cover,
  c" a back cover,
said bearings, held in horizontal position between said front cover and said back cover by the bearing stems extending through the front cover and the back cover, said conveyor being mounted on said post with the bearings being located on opposite sides of said post for vertical movement on the post, said conveyor further comprising d" a lower horizontal hand integral to said conveyor and extending horizontally to a position directly beneath the location of said upper hand,
  e" boxed horizontal twin bearing races having a raised divider between said races,
  f" twin bearings having a common stem on which said bearings are mounted in conjunction with said boxed horizontal twin bearing races,
 g' a hand lever of predetermined size and length pivotally attached at a predetermined location to said carriage, having an end of said lever pivotally attached to said stem of said twin bearings, said lever further having a handle on an opposite end of said lever whereby manual downward pressure on said handle end of said lever will cause said lower hand to advance upward toward the bottom surface of said upper hand, and upward manual pressure on said handle will cause said lower hand to retreat from the bottom surface of said upper hand, said bag apparatus being positioned between said upper hand and said lower hand, and held in place by the straps attached to said upper hand, whereby manual upward and downward pressure on said handle end will cause said bag apparatus to alternately force said air or oxygen into a patient's lungs and to eject said air or oxygen from a patient's lungs,
said device further comprising means for attaching the mechanical means to said bed.

2. The method of resuscitating a patient comprising: providing a substantially flat base, an apparatus mechanically joined to and supported by said base, said apparatus comprising a bag, a valve, a mask, and an endotracheal tube, each of a predetermined size, a supply of a predetermined amount of oxygen and of air, mechanical means mechanically attached to and supported by said base for alternately compressing and releasing the bag of said apparatus, further comprising: providing a a portable stand comprising
 a' a vertical column,
 b' a bottom horizontal clamp segment,
 c' a vertically movable, slidably mounted upper horizontal clamp segment,
 d' means for securing said upper horizontal clamp to said vertical column at predetermined locations, said vertical column, being of predetermined size and length, and being integral to said bottom horizontal clamp segment, extends upward from said bottom clamp segment through said upper horizontal clamp segment, b means for clamping said stand to a horizontal, rigid foundation for supporting said patient, c a slidable carriage comprising
 a' a tubular body of predetermined size and length having a base and having an upper end integral thereto and being mounted on said column,
 b' a horizontal flat platform having a top surface comprising a central area, said platform of predetermined dimensions, integral to said tubular body and located at the base of said tubular body,
 c' an upper horizontal hand integral to said tubular body and located at the upper end of said tubular body, d a square shaped vertical post of predetermined size and length located in the central area of the top surface of said platform and extending vertically to the bottom surface of said upper horizontal hand, e means for releasably securing said post to said platform and to said upper hand, f a rectangularly shaped conveyor comprising
- a' a plurality of bearings having bearing stems,
- b' a front cover,
- c' a back cover, said bearings, held in horizontal position between said front cover and said back cover by the bearings stems extending through the front cover and the back cover, said conveyor being mounted on said post with the bearings being located on opposite sides of said post for vertical movement on the post, said conveyor further comprising
- d' a lower horizontal hand integral to said conveyor and extending horizontally to a position directly beneath the location of said upper hand,
- e' boxed horizontal twin bearing races having a raised divider between said races,
- f' twin bearings having a common stem on which said bearings are mounted in conjunction with said boxed horizontal twin bearing races, g a hand lever of predetermined size and length pivotally attached at a predetermined location to said carriage, having an end of said lever pivotally attached to said stem of said twin bearings, said lever further having a handle on an opposite end of said lever whereby manual downward pressure on said handle end of said lever will cause said lower hand to advance upward toward the bottom surface of said upper hand, and upward manual pressure on said handle will cause said lower hand to retreat from the bottom surface of said upper hand, said bag apparatus being positioned between said upper hand and said lower hand, and held in place by the straps attached to said upper hand, whereby manual upward and downward pressure on said handle end will cause said bag apparatus to alternately force said air or oxygen into a patient's lungs and to eject said air or oxygen from a patient's lungs, said method of resuscitating a patient comprising the following steps:
- a' immobilizing a patient into a supine position on said substantially flat bed,
- b' manually connecting said bag, valve, mask apparatus containing a supply of air or oxygen to a patient's mouth,
- c' manually operating said mechanical means for alternately compressing and releasing the bag of said apparatus a predetermined degree of compression and relaxation whereby a predetermined mount of said air or said oxygen is alternately forced into and ejected from a patient's lungs.

* * * * *